US010568927B2

(12) United States Patent
Fein et al.

(10) Patent No.: US 10,568,927 B2
(45) Date of Patent: *Feb. 25, 2020

(54) METHODS AND COMPOSITIONS COMPRISING DESMOPRESSIN IN COMBINATION WITH A BETA-3-ADRENERGIC RECEPTOR AGONIST (71) Applicant: Serenity Pharmaceuticals, LLC, Milford, PA (US)

(72) Inventors: Seymour H. Fein, New Canaan, CT (US); Samuel Herschkowitz, Brooklyn, NY (US)

(73) Assignee: Serenity Pharmaceuticals LLC, Milford, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/811,384

(22) Filed: Nov. 13, 2017

(65) Prior Publication Data

US 2018/0289769 A1 Oct. 11, 2018

Related U.S. Application Data (63) Continuation of application No. 14/338,554, filed on Jul. 23, 2014, now Pat. No. 9,814,753.

(60) Provisional application No. 61/857,431, filed on Jul. 23, 2013.

(51) Int. Cl.
| A61K 31/426 | (2006.01) |
| A61K 38/08 | (2019.01) |
| A61K 38/11 | (2006.01) |
| A61K 38/095 | (2019.01) |
| A61K 9/00 | (2006.01) |
| A61K 45/06 | (2006.01) |
| A61K 47/08 | (2006.01) |

(52) U.S. Cl.
CPC .......... *A61K 38/095* (2019.01); *A61K 9/0043* (2013.01); *A61K 31/426* (2013.01); *A61K 38/08* (2013.01); *A61K 45/06* (2013.01); *A61K 47/08* (2013.01)

(58) Field of Classification Search
CPC ...... A61K 31/426; A61K 38/08; A61K 38/11; C07D 277/40; C07K 7/16
See application file for complete search history.

(56) References Cited

U.S. PATENT DOCUMENTS

| 3,497,491 A | 2/1970 | Zaoral et al. |
| 3,989,816 A | 11/1976 | Rajadhyaksha |
| 4,316,893 A | 2/1982 | Rajadhyaksha |
| 4,405,616 A | 9/1983 | Rajadhyaksha |
| 4,557,934 A | 12/1985 | Cooper |
| 4,783,450 A | 11/1988 | Fawzi et al. |
| 5,023,252 A | 6/1991 | Hseih |
| 5,534,496 A | 7/1996 | Lee et al. |
| 6,342,251 B1 | 1/2002 | Illum et al. |
| 6,558,695 B2 | 5/2003 | Luo et al. |
| 6,939,324 B2 | 9/2005 | Gonnelli et al. |
| 7,112,561 B2 | 9/2006 | Gyurik et al. |
| 7,182,747 B2 | 2/2007 | Kwon |
| 7,244,703 B2 | 7/2007 | Gyurik et al. |
| 7,335,186 B2 | 2/2008 | O'Neil |
| 7,405,203 B2 | 7/2008 | Fein |
| 7,579,321 B2 | 8/2009 | Fein |
| 7,750,029 B2* | 7/2010 | Takasu ................. C07D 277/40 514/370 |
| 7,799,761 B2 | 9/2010 | Fein |
| 8,143,225 B2 | 3/2012 | Fein |
| 8,399,410 B2 | 3/2013 | Herschkowitz et al. |
| 9,375,530 B2 | 6/2016 | Herschkowitz et al. |
| 9,539,302 B2 | 1/2017 | Fein |
| 9,814,753 B2* | 11/2017 | Fein ..................... A61K 9/0043 |
| 9,925,232 B2 | 3/2018 | Fein et al. |
| 2004/0138098 A1* | 7/2004 | Fein ..................... A61K 9/0056 514/10.9 |
| 2009/0042970 A1* | 2/2009 | Herschkowitz ... A61M 37/0015 514/423 |
| 2010/0056436 A1 | 3/2010 | Fein |
| 2010/0160214 A1 | 6/2010 | Fein et al. |
| 2011/0144055 A1 | 6/2011 | Rozmanith et al. |
| 2012/0015880 A1 | 1/2012 | Fein |
| 2012/0149643 A1* | 6/2012 | Fein ..................... A61K 9/0043 514/10.9 |
| 2012/0202819 A1* | 8/2012 | Edmondson ......... A61K 31/137 514/248 |
| 2012/0322734 A1 | 12/2012 | Fein |

(Continued)

FOREIGN PATENT DOCUMENTS

| CA | 2605224 A1 | 10/2006 |
| CN | 101648017 A | 2/2010 |

(Continued)

OTHER PUBLICATIONS

Bhide et al. Use of mirabegron in treating overactive bladder. International Urogynecological Journal. Mar. 13, 2012, vol. 23, pp. 1345-1348. (Year: 2012).*
Anonymous, (2011), "Document Info—The Management of nocturia in adults with lower urinary tract symptoms," Quick Books Docstoc, Dec. 27, 2011, Retrived from the Internet URL http://www.docstoc.com/docs/109695408/The-Management-of-Nocturia-in-Adults-With-Lower-Urinary-Tract-Symptoms [retrieved on Sep. 2, 2014].
Bae et al., (2013) "Desmopressin Add-On Therapy for Refractory Nocturia in Men Receiving ?-Blockers for Lower Urinary Tract Symptoms," J. Urology, 190:180-186.
Bhide et al., (2012), 'Use of Mirabegron in Treating an Overactive Bladder,' Int Urogynecol J, 23(10):1345-1348.
International Search Report for International Application No. PCT/US2014/047899 (Form ISA/201) dated Sep. 10, 2014 (4 pages).

(Continued)

Primary Examiner — Jeffrey E. Russel
(74) Attorney, Agent, or Firm — Goodwin Procter LLP (57) ABSTRACT The invention provides methods and compositions for use of desmopressin in combination with a beta-3-adrenergic receptor agonist. The methods and compositions are useful in the treatment of nocturia and other urinary frequency disorders.

22 Claims, 2 Drawing Sheets (56) References Cited

U.S. PATENT DOCUMENTS

| | | | |
|---|---|---|---|
| 2013/0172277 A1* | 7/2013 | Caltabiano | A61K 45/06 514/23 |
| 2013/0196956 A1 | 8/2013 | Dill et al. | |
| 2013/0251786 A1 | 9/2013 | Li et al. | |
| 2015/0031614 A1 | 1/2015 | Fein et al. | |
| 2016/0220489 A1 | 8/2016 | Fleming et al. | |
| 2016/0303185 A1 | 10/2016 | Herschkowitz et al. | |
| 2018/0289769 A1 | 10/2018 | Fein et al. | |

FOREIGN PATENT DOCUMENTS

| | | |
|---|---|---|
| JP | 2008535877 A | 9/2008 |
| WO | WO-1992/16213 A1 | 10/1992 |
| WO | WO-2004/041153 A2 | 5/2004 |
| WO | WO-2005/046707 A1 | 5/2005 |
| WO | WO-2007/072156 A1 | 6/2007 |
| WO | WO-2007/083640 A1 | 7/2007 |
| WO | WO-2009/021007 A1 | 2/2009 |
| WO | WO-2010/075266 A2 | 7/2010 |
| WO | WO-2010/075327 A1 | 7/2010 |
| WO | WO-2010/147981 A1 | 12/2010 |
| WO | WO-2013/0142274 A1 | 9/2013 |
| WO | WO-2014/079922 A1 | 5/2014 |
| WO | WO-2015/013453 A1 | 1/2015 |
| WO | WO-2016/081772 A1 | 5/2016 |

OTHER PUBLICATIONS

Nam, Sang Gan et al., (2004), "Efficacy of Desmopressin in Treatment of Adult Nocturia," Korean J. Urol., 45:49-55.
Ohlstein EH et al., (2012), 'A Multicenter, Double-blind, Randomized, Placebo-controlled Trial of the ?3-Adrenoceptor Agonist Solabegron for Overactive Bladder,' Eur Urol, 62(5):834-40.
Russo A et al., (2014), 'Latest Pharmacotherapy Options for Benign Prostatic Hyperplasia,' Exp Opin Pharmacother, 15(16):2319-28.
Sacco E and Bientinesi R, (2012), 'Mirabegron: A Review of Recent Data and its Prospects in the Management of Overactive Bladder,' The Adv Urol, 4(6):315-24.
Son, Joung Hwan, (2011), "The Management of nocturia in adults with lower urinary tract symptoms," Pundang Jesaeng Hospital, Dec. 27, 2011, Retrived from the Internet URL http://www.docstoc.com/docs/109695408/The-Management-of-Nocturia-in-Adults-With-Lower-Urinary-Tract-Symptoms [retrieved on Sep. 2, 2014].
Van Doorn et al., (2011), "Nocturia in older men," Maturitas, 71:8-12.
Wang CJ et al., (2011), 'Low Dose Oral Desmopressin for Nocturnal Polyuria in Patients with Benign Prostatic Hyperplasia: A Double-blind, Placebo Controlled, Randomized Study,' J Urol, 185(1):219-23.
Written Opinion of the International Searching Authority for International Application No. PCT/US2014/047899 (Form ISA/201) dated Sep. 10, 2014 (6 pages).
Chozai to Joho (2012),19(4):108-114 (In Japanese with partial English translation).
Nichi-Yaku-Ri-Shi (2012), (Journal of Pharmacological Sciences), 139: 219-225 (In Japanese with partial English translation).

* cited by examiner

METHODS AND COMPOSITIONS COMPRISING DESMOPRESSIN IN COMBINATION WITH A BETA-3-ADRENERGIC RECEPTOR AGONIST

CROSS-REFERENCE TO RELATED APPLICATIONS

This application is a continuation of U.S. patent application Ser. No. 14/338,554, filed Jul. 23, 2014, issued as U.S. Pat. No. 9,814,753, which claims the benefit of and priority to U.S. Provisional Patent Application No. 61/857,431, filed Jul. 23, 2013.

FIELD OF THE INVENTION

The invention provides methods and compositions for use of desmopressin in combination with a beta-3-adrenergic receptor agonist. The methods and compositions are useful in the treatment of nocturia and other urinary frequency disorders.

BACKGROUND

Nocturia and other urinary frequency disorders affect a significant portion of the human population. Patients with nocturia experience interruption in sleep due to the need to get up during the night to urinate. Patients suffering from overactive bladder often experience urge incontinence, urgency of urination, and higher urinary frequency. Overactive bladder can be caused by uncontrolled contractions of the bundles of smooth muscle fibers forming the muscular coat of the urinary bladder (the detrusor muscle) during the filling phase of the bladder and is more prevalent in elderly adults.

Compositions and methods for treating nocturia and other urinary frequency disorders have been described. For example, U.S. Pat. Nos. 7,579,321; 7,799,761; and 8,143,225 describe pharmaceutical compositions and methods using a low dosage of desmopressin. U.S. patent application publication US 2009/0042970 describes treating nocturia and other urinary frequency disorders using, for example, transdermal administration of desmopressin. Also, U.S. patent application publication US 2012/0015880 describes treating nocturia and other urinary frequency disorders using, for example, intranasal administration of desmopressin.

One of the challenges in treating nocturia and other urinary frequency disorders using desmopressin is achieving a therapeutic, but non-toxic, blood plasma concentration of desmopressin. Administering a dose of desmopressin that is too large can have severe side effects, such as hyponatremia potentially resulting in seizures or death of the patient. As such, the need exists for compositions and methods which have improved safety profiles and/or improved efficacy using a lower dosage of desmopressin. The present invention addresses this need and provides other related advantages.

SUMMARY

The invention provides methods and compositions for use of desmopressin in combination with a beta-3-adrenergic receptor agonist. This combination therapy provides benefits to human subjects, especially adult males, suffering from disorders associated with or featuring undesirable voiding of the subjects' bladder or frequent urge to void. Such persons may suffer from overproduction of urine, inadequate urine concentration, low urine osmolality, excessive frequency of urination (e.g., excessive frequency of urination associated with central diabetes insipidus), adult primary nocturnal enuresis, nocturia, over-active bladder syndrome (OAB), urinary urgency and frequency during waking hours, incontinence, or unwanted production of urine resulting in urine leakage at rest or by exertion or stress. The desmopressin and beta-3-adrenergic receptor agonist are administered to the subject such that both exert physiological activity during an overlapping time period. Exemplary beta-3-adrenergic receptor agonists include, for example, amibegron, fasobegron, mirabegron, ritobegron, solabegron, BRL-37344, CL-316,243, GS-332, KRP-204, L-796568, and pharmaceutically acceptable salts thereof.

Accordingly, one aspect of the invention provides a method of inhibiting the urge to urinate in a human subject over an interval of about two hours to no more than about seven hours. The method comprises administering to a human subject in need thereof an effective amount of desmopres sin and a beta-3-adrenergic receptor agonist so that both exert physiological activity during an overlapping time period. The dosage of desmopressin and/or beta-3-adrenergicreceptor agonist and/or the dosing regimen may be adjusted so that the method inhibits the urge to urinate in a human subject over an interval of about 4 hours to about 7 hours. The desmopressin is administered at a dosage such that the subject does not experience-hyponatremia, a harmful condition in which the sodium concentration in the subject's plasma is too low, e.g., below about 135 mmol/L. Hyponatremia is avoided provided the maximum dose of desmopres sin in the blood is less than 10 pg/ml, preferably less than 5 pg/ml, and most preferably less than 5 pg/ml, e.g., 2 or 3 pg/ml. Severe hyponatremia can result in electrolyte abnormalities that can cause cardiac arrhythmias, heart attack, seizures, and/or stroke.

Another aspect of the invention provides a method of inducing an antidiuretic effect in a human subject. The method comprises administering to a human subject in need thereof an effective amount of desmopressin and a beta-3-adrenergic receptor agonist so that both exert physiological activity during an overlapping time period.

Another aspect of the invention provides a pharmaceutical composition comprising desmopressin, a beta-3-adrenergic receptor agonist, and a pharmaceutically acceptable carrier. In certain embodiments, the pharmaceutical composition is formulated for transmucosal administration, e.g., buccal or nasal administration to a human subject. In other embodiments the composition is formulated as a transdermal or intradermal patch. In other embodiments the beta-3-adrenergic receptor agonist is taken orally while the desmopressin is taken transmucosally, e.g., sublingually or intranasally.

DETAILED DESCRIPTION OF THE INVENTION

The invention provides methods and compositions for use of desmopressin in combination with a beta-3-adrenergic receptor agonist. This combination therapy provides benefits to subjects suffering from disorders associated with or featuring undesirable voiding of the subjects' bladder of frequent urge to void. Such subjects may suffer from overproduction of urine, inadequate urine concentration, low urine osmolality, excessive frequency of urination (e.g., excessive frequency of urination associated with central diabetes insipidus), adult primary nocturnal enuresis, nocturia, urinary urgency and frequency during waking hours, over-active bladder syndromes (OAB), incontinence, or unwanted production of urine resulting in urine leakage at rest or by exertion or stress. The desmopressin and beta-3-adrenergic receptor agonist are administered to the subject such that both exert physiological activity during an overlapping time period. The agonist may be administered at doses below those used in current clinical practice, for the treatment of Benign Prostate Hyperplasia (BPH).

Various aspects of the invention are set forth below in sections; however, aspects of the invention described in one particular section are not to be limited to any particular section.

Definitions

To facilitate an understanding of the present invention, a number of terms and phrases are defined below.

The terms "a," "an" and "the" as used herein mean "one or more" and include the plural unless the context is inappropriate As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for therapeutic use in vivo or ex vivo.

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$, (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The terms "subject" and "patient" are used interchangeably and refer to humans, especially adult male humans.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

I. Therapeutic Methods

The invention provides therapeutic methods using desmopressin in combination with a beta-3-adrenergic receptor agonist. This combination therapy provides benefits to subjects suffering from disorders associated with or featuring undesirable frequent urges to void the subjects' bladder. As described above, such subjects may suffer from overproduction of urine, inadequate urine concentration, low urine osmolality, OAB, excessive frequency of urination (e.g., excessive frequency of urination associated with central diabetes insipidus), adult primary nocturnal enuresis, nocturia, urinary urgency and frequency during waking hours, incontinence, or unwanted production of urine resulting in urine leakage at rest or by exertion or stress. The desmopressin and beta-3-adrenergic receptor agonist are administered to the subject such that both exert physiological activity during an overlapping time period. Desirably, administration of desmopressin and the beta-3-adrenergic receptor agonist results in a synergistic effect. Exemplary benefits from such a synergistic effect include improved reduction in a subject's urge to urinate and/or a reduction in the amount of desmopressin needed to achieve a therapeutic effect. Furthermore, administration of reduced amounts of the beta-3-adrenergic receptor agonist relative to the doses used clinically to treat BPH mean that side effects of these drugs are reduced.

One aspect of the invention provides a method of inhibiting the urge to urinate in a human subject over an interval of about two hours to no more than about eight hours. The method comprises administering to a human subject in need thereof an effective amount of desmopressin and a beta-3-adrenergic receptor agonist so that both exert physiological activity during an overlapping time period. The dosage of desmopressin and/or beta-3-adrenergic receptor agonist and/or the dosing regimen may be adjusted so that the method inhibits the urge to urinate in a human subject over certain intervals. For instance, in certain embodiments, the method inhibits the urge to urinate in a human subject for an interval of about 4 hours to about 6 or 7 hours. Various embodiments of the method (e.g., dosage and route of administration of desmopressin, the beta-3-adrenergic receptor agonist, the target patient population, and exemplary benefits of the combination therapy) are described in the sections below.

Another aspect of the invention provides a method of inducing an antidiuretic effect in a human subject. The method comprises administering to a human subject, e.g., an adult male, in need thereof an effective amount of desmopressin and a beta-3-adrenergic receptor agonist so that both exert physiological activity during an overlapping time period. The method can be further characterized according to the interval over which an antidiuretic effect is provided. For instance, in certain embodiments, an antidiuretic effect is achieved over an interval of about two hours to no more than about seven or eight hours. In certain other embodiments, the antidiuretic effect is achieved over an interval of about four hours to about six hours. Various embodiments of the method (e.g., dosage and route of administration of desmopressin, dosage and route of administration of the beta-3-adrenergic receptor agonist, patient population, and exemplary benefits of the combination therapy) are described in the sections below.

In certain embodiments, the method comprises administering to the subject a beta-3-adrenergic receptor agonist on a daily basis for a period of at least a month and administering desmopressin before the subject retires to sleep. In certain other embodiments, the method comprises administering to the subject a beta-3-adrenergic receptor agonist at a dose level lower than its smallest drug label recommended dose for treatment of BPH and administering desmopressin before the subject retires to sleep. In yet other embodiments, the method comprises administering to the subject as a mixture before the subject retires to sleep desmopressin and a beta-3-adrenergic receptor agonist at a dose level lower than the smallest drug label recommended dose of said agonist for treatment of BPH.

Desmopressin

The term "desmopressin" refers to 1-desamino-8-D-arginine vasopressin and includes the free base form and pharmaceutically acceptable salts and hydrates thereof. One exemplary salt form is an acetate salt. Desmopressin, 1-desamino-8-D-arginine vasopressin monoacetate, also known as DDAVP, is described in, for example, U.S. Pat. No. 3,497,491, and is commercially available as a prescription medication sold, for example, under the names DesmoMelt, Stimate, Minirin® and DESMOSPRAY®. Desmopressin as an active pharmaceutical ingredient also is available commercially for formulation into new drug dose forms and compositions. The dosage of desmopressin administered to a human subject can be selected based on the weight of the subject and the desired duration over which a therapeutic effect is desired. The dosage can be characterized according to the blood plasma concentration of desmopressin achieved.

Accordingly, therapeutic methods described herein can be characterized according to the blood plasma concentration of desmopressin achieved. In certain embodiments, the administering achieves in the human subject a blood plasma concentration of desmopressin that does not exceed 15 pg/mL. In certain other embodiments, the administering achieves in the human subject a blood plasma concentration of desmopressin in the range of about 0.2 pg/mL to about 5 pg/mL. In yet other embodiments, the administering achieves in the human subject a blood plasma concentration of desmopressin in the range of about 0.5 pg/mL to about 2.5 pg/mL. In yet other embodiments, the administering achieves in the human subject a blood plasma concentration of desmopressin in the range of about 0.5 pg/mL to about 1.5 pg/mL. Generally, the amount of desmopressin that reaches the bloodstream from administration of a given specific dose form should not exceed 2 ng/kg of body weight, and can be as low as 0.5 ng/kg, 1.0 ng/kg, or 1.5 ng/kg.

Desmopressin can be administered using traditional routes of administration. For example, in certain embodiments, desmopressin is administered transdermally, intradermally, transmucosally, or even possibly orally, although the variability of the bioavailability of oral doses is so great that consistent very low blood concentrations are hard or impossible to achieve reproducibly. In certain other embodiments, desmopressin is administered transdermally, intradermally, or transmucosally. In yet other embodiments, desmopressin is administered transdermally. In still other embodiments, desmopressin is administered intranasally.

When desmopressin is administered transdermally or intradermally, the method can be characterized according to the rate at which desmopressin is passed through the skin of a human subject. For example, in certain embodiments, desmopressin is administered at a first flux rate sufficient to achieve rapidly a desired blood plasma concentration of desmopressin, e.g., less than five, preferably less than 2 pg/ml, and then at a second, lower flux rate sufficient to maintain the first attained blood plasma concentration for a desired interval, e.g., six hours. In certain embodiments, the method is further characterized by a flux range, such as where desmopressin is administered at a flux rate ranging from about 5 ng/hour to about 35 ng/hour. In yet other embodiments, desmopressin is administered at a flux rate ranging from about 5 ng/hour to about 35 ng/hour. In still other embodiments, desmopressin is administered at a flux rate ranging from about 5 ng/hour to about 15 ng/hour.

Various devices and methods for administering desmopressin have been described previously and are contemplated for use in the present invention. See, for example, U.S. Patent Application Publication Nos. US 2009/0042970 and US 2012/0015880, each of which are hereby incorporated by reference. One device that may be used to administer desmopressin has a depot containing a solution of desmopressin in a pharmaceutically acceptable carrier. An interface member for application to the skin of a patient, such as a permeable pad for attachment to the skin, or one or an array of microneedles, are in fluid communication with the depot. The devices comprise various means for delivering the desmopressin solution from the depot to the interface member and downstream intradermally or transdermally to the blood of a patient. The flux rate of the desmopressin is controlled by setting the concentration of desmopressin in the depot, in combination with controlling either the rate of flow of solution from the depot, the rate of flow of solution to the interface member, the rate of flow of solution from the interface member into the body of the patient, or by exploitation of some combination of these control points. In any event, the influx rate is controlled to be sufficient to establish a desmopressin concentration in the blood of the patient just above the water channel activation threshold, e.g., within the range of 0.1 to about 2.5 pg/ml, advantageously no greater than 1, 1.5, 2, or 2.5 pg/ml. The flux rate in any case is insufficient to induce a desmopressin concentration in the blood of the patient to a level greater than about 10 pg/ml. The flux rate may be between about 5, 10, 15, 20, 25, or 30 to 35 ng/hr (i.e., 5000, 10,000, 15,000, 20,000, 25,000, or 30,000 to 35,000 pg/hr), advantageously about 10-20 ng/hr or 20-35 ng/hr, more advantageously about 5-15 ng/hr, so as to establish the desired blood concentration for a reasonable, predetermined time before the patient or the device shuts off desmopressin flow.

The dosage of desmopressin and/or duration of a therapeutic blood plasma concentration of desmopressin necessary to achieve a therapeutic effect is desirably less when desmopressin is used together with the beta-3-adrenergic receptor agonist than when desmopressin is administered alone, and the urge to void is reduced as compared to when the beta-3-adrenergic receptor agonist is administered alone. For example, in certain embodiments, the beta-3-adrenergic receptor agonist may reduce the urge to urinate for a period of time after which the desmopressin blood plasma concentration drops below the threshold necessary to achieve antidiuresis (activation of water channels in the kidney). As another example, the physiological effect of the beta-3-adrenergic receptor agonist in combination with less urine filling the bladder during the interval of induced antidiuresis together have the effect of decreasing the patient's urge to urinate.

The flux rate of desmopressin may be preferably set so that, given the desired blood concentration and the known clearance rate of desmopressin (half-life of about 1.5 to 2.0 hours), the patient reaches the desired low but supra-threshold blood concentration in a reasonable time, e.g., less than an hour (and generally, the sooner, the better), and is maintained within a low dose range just above the activation threshold (approximately within the range of 0.5 to 1.5 pg/ml) for a desired time period (e.g., two hours for a workout, or 4-6 hours or 5-8 hours for treatment of nocturia). Termination of the flux by automatic or manually actuated mechanisms built into the device, or by removal of the device from contact with the skin, results in normal drug clearance echanisms of the body of the patient rapidly reducing the low concentration to a still lower concentration, below the activation threshold.

The interface member of the device may comprise a desmopressin solution-permeable membrane defining a surface for contact with the skin of the patient. The desmopressin solution-permeable surface permits delivery of the desmopressin from the depot through or to the skin of the patient. For highest bioavailability and precision of delivery, intradermal delivery is preferred. Intradermal delivery permits direct delivery to a vascularized compartment resulting in rapid absorption into the systemic circulation and correspondingly rapid on/off effects. While transdermal delivery is contemplated, its use is more subject to variable bioavailability due to the stratum corneum functioning as a physical barrier to drug reaching the epidermis, and to the creation of a depot of drug in the epidermis.

Accordingly, transdermal delivery methods and devices can benefit from techniques that reduce the efficacy of the stratum corneum as a barrier to drug entry. These include, for example, mechanical methods for removing portions of the stratum corneum before applying a transdermal desmopressin delivery device. The skin can also be "micropunctured" to introduce "micropassages" or "microfissures" across the stratum corneum, to enhance subsequent transdermal delivery, e.g. by one or more microneedles as described below.

The permeability of the stratum corneum can also be enhanced by treatment with a chemical permeability enhancer, such as dimethylsulfoxide, decylmethylsulfoxide, diethylene glycol monomethyl ether, diethyleneglycol monoethyl ether, sodium laurate, sodium lauryl sulfate, cetyltrimethylammonium bromide, benzalkonium choride, lecithin (see, for example, U.S. Pat. No. 4,783,450, the teachings of which are hereby incorporated by reference), 1-n-dodecylazacycloheptan-2-one (see, for example, U.S. Pat. Nos. 3,989,816; 4,316,893; 4,405,616; and 4,557,934, the teachings of which are hereby incorporated by reference), ethanol, propanol, octanol, benzyl alcohol, lauric acid, oleic acid, valeric acid, isopropyl myristate, isopropyl palmitate, methylpropionate, ethyl oleate, propylene glycol, ethylene glycol, glycerol, butanediol, polyethylene glycol, polyethylene glycol monolaurate, urea, hydroxide (see, for example, U.S. Pat. No. 6,558,695, the teachings of which are hereby incorporated by reference), dimethylacetamide, dimethylformamide, 2-pyrrolidone, 1-methyl-2-pyrrolidone, ethanolamine, diethanolamine, triethanolamine, salicylic acid, citric acid, succinic acid, and permeability enhancing peptides (see, for example, U.S. Pat. No. 5,534,496, the teachings of which are hereby incorporated by reference).

An efficient means of desmopressin delivery from the depot to the skin is intradermal administration, via an interface member comprising one or more microneedles which penetrate the stratum corneum of the patient and enable fluid communication between the depot and the epidermis or direct contact with surfaces or cavities in the microneedles coated with or containing desmopressin. The length and size of the microneedles are adequate to penetrate the stratum corneum but small enough to produce little if any sensation for the patient. For example, suitable lengths are about 0.3 to 1.5 mm, advantageously between about 0.8 to 1.1 mm. An example of a single needle device is provided in U.S. Pat. No. 6,939,324, the teachings of which are herein incorporated by reference.

A plurality of microneedles, e.g., in an array, may be desirable if more surface area for delivery, or a more flexible patch, is desired. The microneedles may each have a channel that transports fluid from the depot to the needle end, or the microneedles may otherwise allow for fluid delivery from the depot, e.g., with perforated or porous walls. Alternatively, the microneedles may be coated with a desmopressin preparation or contain a film or matrix of desmopressin in cavities or in the material structure of the microneedle itself, to provide a burst of desmopressin upon application so as to aid rapid achievement of the threshold activating concentration, optionally with desmopressin solution passing through the needles to help achieve, or to maintain the desired concentration.

The use of dissolvable microneedles is also contemplated, as their use avoids, in some cases, pain and/or irritation caused by metal needles or piercing elements. U.S. Pat. No. 7,182,747, for example, discloses "solid solution perforators" which may be adapted for use in the inventions disclosed herein. In contrast to conventional hollow needle technologies, these microneedles are made from a solid matrix of dissolvable or biodegradable material that optionally holds one or more selected drugs and is formed into one or more perforators.

Another device for delivering desmopressin is a patch that the user applies before sleep, or before some other interval of activity where the patient desires to interrupt urine production. The patch may but need not necessarily include an active solution flow control mechanism, e.g., with a user-selectable timing function, so the user can choose the length of time he wishes to have normal urine production suppressed, i.e., in the case of sleep, roughly equivalent to or shorter than the desired sleep time. The patient removes the patch from its packaging, sets the delivery time if necessary, and applies the patch to an area of the skin. Desmopressin delivery at the levels and rates described herein then begins, and urine production is suppressed for the desired time. When the flow controller is shut off, the patch is removed, or the desmopressin depot is exhausted, normal urine production returns quickly. In a preferred simple version of the device, the amount of desmopressin in the depot and its engineered flux rate through exhaustion of the depot fixes the delivery time, e.g., five to seven hours, with termination of flux corresponding simply to exhaustion of the patch delivery. Thus, the patient can sleep without having to wake perhaps repeatedly during the sleep hours, or engage in other activity without concern about involuntary voiding.

Turning to the drawings, the operation of exemplary devices will be described.

Figure 1:
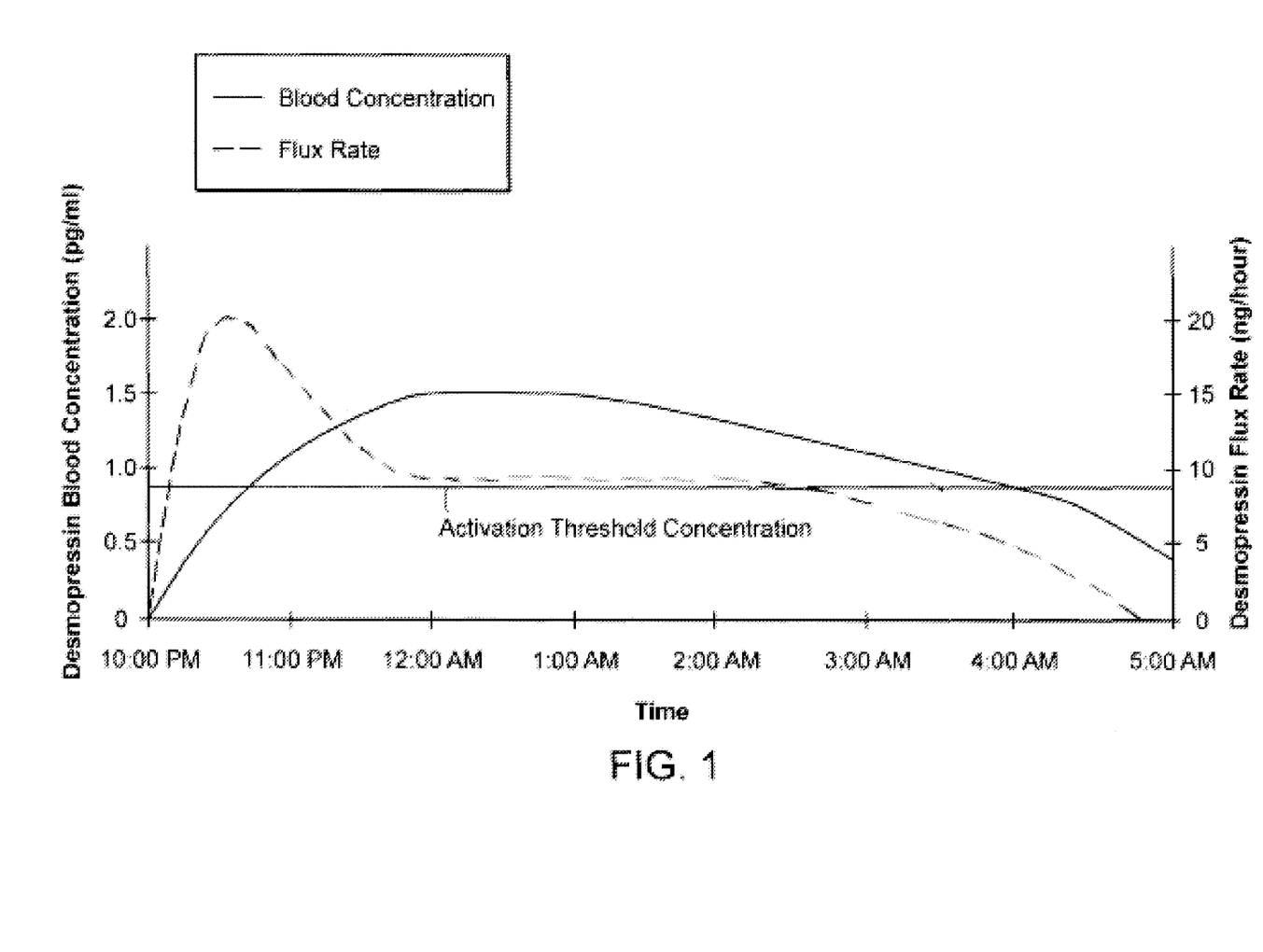
FIG. 1 is a graph of desmopressin blood concentration and variable flux rate versus time illustrating a 7-hour operation of a device and method.

FIG. 1 illustrates operation of an exemplary embodiment of the invention in treating a patient for whom shutting off urine production is desired, e.g., treating nocturia. A device according to the invention that delivers a low dosage/low variable flux of desmopressin to a patient is affixed to the skin of the patient, the patient urinates, and the device is activated at 10:00 P.M. FIG. 1 shows illustrative and exemplary blood desmopressin concentrations and the flux rates for this patient at various times following application or activation of the device. At one hour (11:00 P.M.), the desmopressin flux rate has peaked at about 20 ng/hr and has raised the patient's blood desmopressin concentration to over about 1.0 pg/ml, i.e., above the concentration sufficient to activate kidney water channels and to induce an antidiuretic effect (here illustrated as being at a blood concentration of about 0.8 pg/ml). At 2 hours (midnight), the flux rate is decreasing slightly but is still in the 20 ng/hr range, and blood desmopressin concentration is elevated to about 1.5 pg/ml. These values decrease slowly but are relatively constant for the next 2.5 to 3 hours. After about 5 hours (3:00 AM), the flux rate has decreased to a level where the activation concentration of desmopressin cannot be sustained. As the flux rate continues to drop, the blood desmopressin concentration falls below the water channel activation level, and urine production commences (here at about 3:45 AM). By 5:00 AM blood concentration is below about 0.5 pg/ml and flux rate has dropped to zero. By 6:00 AM the patient is awake and feels a normal urge to void as urine has been produced for the last hour and a half or so of sleep. During the sleep there is a sustained antidiuretic interval, little or no urine production, and no bothersome or sleep-interrupting urge to void. The flux rate of desmopressin and the blood concentration of desmopressin may be more or less depending on the dosage of beta-3-adrenergic receptor agonist administered to the patient. It is appreciated that the desmopressin and beta-3-adrenergic receptor agonist may be administered to the patient in separate formulations, or the desmopressin and beta-3-adrenergic receptor agonist may be mixed together to form a single formulation that is administered to the patient.

Figure 2:
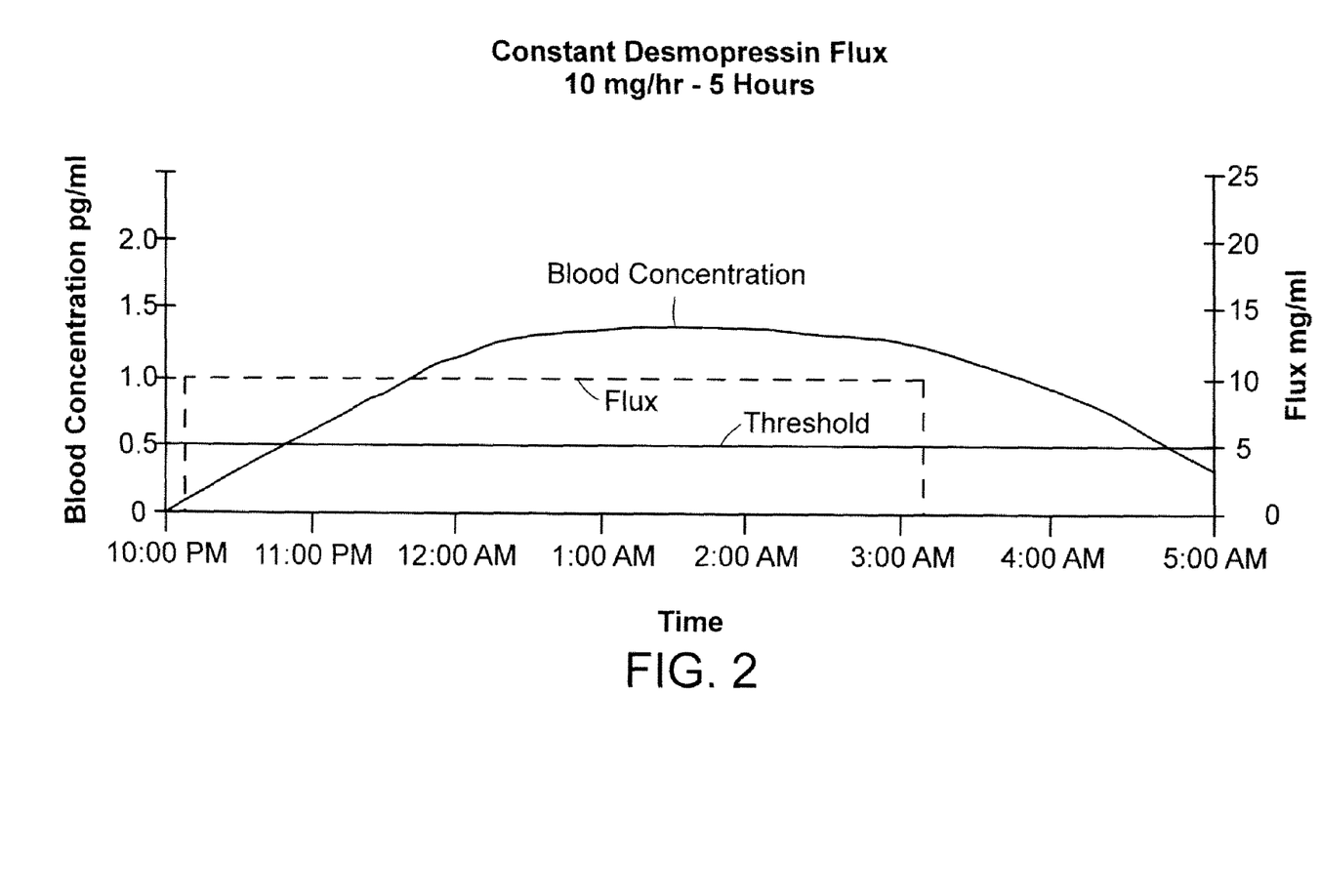
FIG. 2 is a graph of desmopressin blood concentration and constant flux rate versus time illustrating a 7-hour operation of a device and method according to an alternative embodiment.

FIG. 2 illustrates another exemplary embodiment of the invention for treating a patient to shut off urine production, e.g., treating nocturia. A device according to the invention that delivers a low dosage constant flux of desmopressin is affixed to the skin of the patient. The device is activated (if necessary) and the patient urinates at 10:00 PM. FIG. 2 shows illustrative and exemplary blood desmopressin concentrations resulting from a flux of about 10 ng/hr over about a five hour infusion from 10:00 PM to 3:00 AM relative to the threshold blood concentration for desmopressin's antidiuretic effect. Within about an hour from flux initiation the blood desmopressin concentration exceeds the threshold level and begins to exert an antidiuretic effect. The blood concentration approaches a more or less stable range within about two to three hours (between about 1.0 and 1.5 pg/ml) which is sustained during the remainder of the five hour flux until 3:00 AM. At this time the flux is discontinued (e.g., timed out or exhausted). Now the blood desmopressin concentration decreases from clearance mechanisms in accordance with the drug's elimination half-life, falling below the threshold approximately two hours later (5:00 AM). By 7:00 AM the patient has produced urine, and wakes to void. The flux rate of desmopressin and the blood concentration of desmopressin may be more or less depending on the dosage of beta-3-adrenergic receptor agonist administered to the patient.

The foregoing examples are for illustrative purposes only. The activation concentration will of course vary among individuals, as will blood volume. The important principle in the operation of the device is that the antidiuretic effect can be controlled safely, as the diuretic action is maintained by maintaining a low desmopressin concentration by a continuous low influx of the drug, and an interruption of the influx permits the body to rapidly clear the drug and to re-establish normal urine production. This means that the patch devices enhance safety of desmopressin administration, with little or no risk of development of water intoxication when used as directed.

In accordance with the invention, the beta-3-adrenergic receptor agonist may be present in admixture with the desmopressin in the patch devices described above, or with the intranasal dose form disclosed below, but preferably is supplied as a daily oral dose, and is active and present in the blood plasma during the time the desmopressin is present.

An exemplary device for intranasal administration of desmopressin is a safety dispenser for inducing in members of a target patient population an antidiuretic effect while reducing the risk that a member of the population may develop hyponatremia. The dispenser comprises a reservoir having disposed therein a composition comprising a preparation of desmopressin and a nasal membrane permeation enhancer in an amount sufficient to constitute multiple drug doses. The reservoir is in communication with an outlet and is fitted with a pump, preferably a disposable pump, and preferably one that can be actuated manually, such as a squeeze bottle actuated dispenser, or a plunger pump fitted onto a glass bottle. The pump enables serially dispensing multiple metered doses from the reservoir through the outlet in the form of a spray into a nostril or nostrils of a patient so as to deposit a dose of consistent size onto an intranasal mucosal or other surface.

Each spray comprises a multiplicity of droplets, preferably with an average volume distribution in the range of 20 μm for D10 to about 300 μm for D90. This means that about 10% of the droplets are smaller than about 20 μm in diameter and 90% are smaller than 300 μm in diameter. Each spray dose is preferably of a weight and desmopressin concentration such that it comprises between 0.5 ng desmopressin per kilogram of the patient's body weight and 75 ng desmopressin per kilogram of the patient's body weight. The spray is characterized by a desmopressin bioavailability greater than about 5%, that is, between about 5% and 25% of the active in the composition actually enters the patient's bloodstream and contributes to the drug effect, and the remainder is degraded, typically by digestion. Generally, the higher the bioavailability of a spray, the less desmopressin per spray needs to be delivered into a nasal cavity, and vice versa, the goal being to achieve more consistently a target desmopressin maximum blood concentration ($C_{max}$) in members of the patient population.

The combination of properties of the spray dispenser and the composition it contains enables respective doses of spray to be effective to restrict the concentration of desmopressin produced in the bloodstream of patients, on a per kilogram basis, to a relatively narrow range, thereby to achieve a relatively consistent, time limited duration of antidiuresis. Stated differently, respective successive spray doses establish in a patient by drug transport across intranasal mucosal membranes a $C_{max}$ of desmopressin which is relatively consistent. The amount of drug delivered to the bloodstream for repeated doses from the same dispenser to the same person preferably should differ no more than 100%, and preferably less than 50%. The dispenser's coefficient of variation is similar to the coefficient of variation of $C_{max}$ produced by serial subcutaneous doses of desmopressin designed to achieve the same target $C_{max}$. Preferably, respective successive spray doses are sufficient to establish in a patient by intranasal delivery a $C_{max}$ of desmopressin having a coefficient of variation within about 50%, more preferably about 25%, of the coefficient of variation of $C_{max}$ produced by a subcutaneous dose of desmopressin designed to achieve the same target $C_{max}$.

The value of the target $C_{max}$ may be varied, depending on the duration of the antidiuretic interval the dispensed composition is designed to induce and the dosage of beta-3-adrenergic receptor agonist. For example, a product designed for a 7-8 hour interval of urine production suppression might be designed to deliver a $C_{max}$ of no more than 15+/−3 pg/ml. Thus, by way of illustration, a 7 hour product might have a bioavailability of 10% and a desmopressin load per spray of 0.75 μg or 750 ng. This would mean that about 75 ng of drug would reach the patient's bloodstream, and that a 70 kg (~155 lb.) adult would receive a dose in his bloodstream of about 1.0 ng/kg, and achieve a target $C_{max}$ of less than about 5 pg/ml. Another embodiment of the same product might have a bioavailability of 8% and a desmopressin load per spray of 2.0 μg or 2000 ng, delivering about 160 ng drug to the patient's bloodstream as an effective dose of 160 ng/75 kg or slightly more than 2 ng/kg, and the target $C_{max}$ of less than about 10 pg/ml. Another exemplary product may be designed for a 3-4 hour urine interruption and might deliver a $C_{max}$ of no more than about 3 pg/ml.

Alternatively, a single dispenser which delivers, e.g., 200 ng or 500 ng per spray, when used in accordance with package insert or physician instructions, may serve to achieve, for example, different durations of antidiuresis in the same person or the same duration of antidiuresis in adults of different weight, simply by varying the number of spays delivered per administration event. Typically, about 20 minutes to an hour after administration of the pharmaceutical composition of the present invention, the mean urine output per minute in a treated individual decreases to less than about 4 ml/minute, preferably less than about 1 ml/min, and stays in this low range for a desired time period, such as 180 minutes, 240 minutes, 300 minutes, 360 minutes, or 420 minutes. About twenty minutes after administration, the mean urine osmolarity is greater than about 300 mOsmol/kg and remains at high concentration for a period of time ranging up to 180 minutes, 240 minutes, 300 minutes, 360 minutes, or 420 minutes.

One important property of the intranasal administration is that it consistently deliver per spray a maximum blood concentration within a relatively narrow time and dose range, and therefore avoid or minimize accidental delivery of a larger dose resulting in a longer than expected antidiuretic effect and the possibility of induction of hyponatremia. Consistent delivery, as the phrase is used herein, should be taken to mean repeatable within a range similar to the range observed when administering very low doses of desmopressin by subcutaneous injection, or perhaps somewhat greater. Such consistency generally is achieved more easily exploiting formulations with higher bioavailability, and accordingly a bioavailability of at least 5%, preferably at least 10%, more preferably at least 15%, and preferably even higher is preferred. Higher bioavailability is achieved by exploiting formulation technology, especially the use of permeation enhancers, and by chemical engineering of the spray composition as disclosed herein.

In one embodiment, the dispenser may further comprise means for blocking dispensing of a second desmopressin spray, or series of sprays above a certain dose, e.g., above about a dose sufficient to produce a blood concentration above about 10 to 12 pg/ml, for a predetermined time interval after dispensing a first dose. This can be achieved passively as a consequence of the design of the spray mechanism as disclosed, for example, in U.S. Pat. No. 7,335,186, the disclosure of which is incorporated herein by reference. Alternatively, an active timer, powered by a battery, mechanical spring, or compressed gas within the dispenser, may be included together with mechanisms known per se designed to preclude a second dispensing until passage of a predetermined interval, e.g., 8 hours, or somewhere between 6 to 24 hours. Such a mechanism can discourage abuse of the product and further minimize the chances that a patient may inadvertently or intentionally self-induce antidiuresis for too long.

Exemplary permeation enhancers for use in the formulation are "Hsieh enhancers" (see U.S. Pat. No. 5,023,252) available commercially from CPEX Pharmaceuticals (formerly Bentley) of Exeter, N.H. Preferred within the class of Hsieh enhancers useful in the articles of manufacture are those disclosed in U. S. Pat. No. 7,112,561 and U.S. Pat. No. 7,112,561, and the currently most preferred are disclosed in U.S. Pat. No. 7,244,703, such as cyclopentadecanolide, known in the trade as CPE-215. Many other enhancers may be used.

In some embodiments, the invention provides uses of the safety dispenser to induce an antidiuretic effect. The dispenser and desmopressin formulation may comprise any of the properties described herein. For example, in one embodiment, the desmopressin $C_{max}$ is directly proportional to the amount of nasally administered desmopressin over a $C_{max}$ ranging from about 0.5 pg/ml to about 10.0 pg/ml. The value of the target $C_{max}$ may be varied, depending on the duration of the antidiuretic interval the dispensed composition is designed to induce and the dosage of beta-3-adrenergic receptor agonist. For example, use of a safety dispenser described herein may produce antidiuresis for less than about 8 hours, less than about 6 hours, for between about 2 and 4 hours, or for between about 4 and 7 hours. Another exemplary use of a product may be designed to deliver a $C_{max}$ in a patient of no more than about 15 pg/ml, 10 pg/ml, 7 pg/ml, or 3 pg/ml.

Beta-3-Adrenergic Receptor Agonists

Beta-3-adrenergic receptor agonists are a class of medicinal agents that are agonists of the beta-3-adrenergic receptor. Examplary beta-3-adrenergic receptor agonists include, for example, amibegron, fasobegron, mirabegron, ritobegron, solabegron, BRL-37344, CL-316,243, GS-332, KRP-204, L-796568, and pharmaceutically acceptable salts thereof. A brief description of these potentially suitable beta-3-adrenergic receptor agonists is provided below.

Amibegron

Amibegron has the chemical name ethyl (((7S)-7-(((2R)-2-(3-chlorophenyl)-2-hydroxyethyl)amino)-5,6,7,8-tetrahydronaphthalen-2-yl)oxy)acetate. A pharmaceutically acceptable salt of amibegron (e.g., amibegron hydrochloride) may be used. Amibegron may be administered via routes known in the art, such as by oral administration. The amount of amibegron or a pharmaceutically acceptable salt thereof administered to the patient can be in the range of, for example, about 1 mg to about 500 mg per day. In certain embodiments, amibegron is administered (e.g., orally) at a daily dosage ranging from about 1 mg to 5 mg, about 5 mg to about 10 mg, about 10 mg to about 25 mg, about 20 mg to about 30 mg, about 30 mg to about 50 mg, about 50 mg to about 100 mg, about 100 mg to about 150 mg, about 150 mg to about 200 mg, about 200 mg to about 250 mg, about 250 mg to about 300 mg, about 300 mg to about 350 mg, about 350 mg to about 400 mg, about 400 mg to about 450 mg, or about 450 mg to about 500 mg.

Fasobegron

Fasobegron has the chemical name 4-[4-[2-[[(2R)-2-(3-chlorophenyl)-2-hydroxy-ethyl]amino]ethyl]phenyl]-2-methoxy-benzoic acid. A pharmaceutically acceptable salt of fasobegron (e.g., fasobegron hydrochloride) may be used. Fasobegron may be administered via routes known in the art, such as by oral administration. The amount of fasobegron or a pharmaceutically acceptable salt thereof administered to the patient can be in the range of, for example, about 1 mg to about 1000 mg per day. In certain other embodiments, fasobegron is administered (e.g., orally) at a daily dosage ranging, for example, from about 1 mg to 5 mg, about 5 mg to about 10 mg, about 10 mg to about 25 mg, about 25 mg to about 50 mg, about 50 mg to about 100 mg, about 100 mg to about 200 mg, about 200 mg to about 300 mg, about 300 mg to about 400 mg, about 400 mg to about 500 mg, about 500 mg to about 600 mg, about 600 mg to about 700 mg, about 700 mg to about 800 mg, about 800 mg to about 900 mg, or about 900 mg to about 1000 mg.

Mirabegron

Mirabegron has the chemical name 2-(2-aminothiazol-4-yl)-4'-(2-((2-hydroxy-2-phenylethyl)amino)ethyl)acetanilide and is commercially available under the trade name Myrbetriq™. A pharmaceutically acceptable salt of mirabegron (e.g., mirabegron hydrochloride) may be used. Mirabegron may be administered via routes known in the art, such as by oral administration. The amount of mirabegron or a pharmaceutically acceptable salt thereof administered to the patient can be in the range of, for example, about 1 mg to about 500 mg per day. In certain embodiments, mirabegron is administered (e.g., orally) at a daily dosage ranging from about 1 mg to 5 mg, about 5 mg to about 10 mg, about 10 mg to about 20 mg, about 20 mg to about 30 mg, about 30 mg to about 50 mg, about 50 mg to about 100 mg, about 100 mg to about 150 mg, about 150 mg to about 200 mg, about 200 mg to about 250 mg, about 250 mg to about 300 mg, about 300 mg to about 350 mg, about 350 mg to about 400 mg, about 400 mg to about 450 mg, or about 450 mg to about 500 mg.

Ritobegron

Ritobegron has the chemical name (4-(2-(((1R,2S)-1-Hydroxy-1-(4-hydroxyphenyl)propan-2-yl)amino)ethyl)-2,5-dimethylphenoxy)acetic acid. A pharmaceutically acceptable salt of ritobegron (e.g., ritobegron hydrochloride) may be used. Ritobegron may be administered via routes known in the art, such as by oral administration. The amount of ritobegron or a pharmaceutically acceptable salt thereof administered to the patient can be in the range of, for example, about 1 mg to about 1000 mg per day. In certain embodiments, ritobegron is administered (e.g., orally) at a daily dosage ranging from about 1 mg to 5 mg, about 5 mg to about 10 mg, about 10 mg to about 25 mg, about 25 mg to about 50 mg, about 50 mg to about 100 mg, about 100 mg to about 200 mg, about 200 mg to about 300 mg, about 300 mg to about 400 mg, about 400 mg to about 500 mg, about 500 mg to about 600 mg, about 600 mg to about 700 mg, about 700 mg to about 800 mg, about 800 mg to about 900 mg, or about 900 mg to about 1000 mg.

Solabegron

Solabegron has the chemical name 3'-((2-((2-(3-chlorophenyl)-2-hydroxyethyl)amino)ethyl)amino)-(1,1'-biphenyl)-3-carboxylic acid. A pharmaceutically acceptable salt of solabegron (e.g., solabegron hydrochloride) may be used. Solabegron may be administered via routes known in the art, such as by oral administration. The amount of solabegron or a pharmaceutically acceptable salt thereof administered to the patient can be in the range of, for example, about 1 mg to about 500 mg per day. In certain embodiments, solabegron is administered (e.g., orally) at a daily dosage ranging from about 1 mg to 5 mg, about 5 mg to about 10 mg, about 10 mg to about 20 mg, about 20 mg to about 30 mg, about 30 mg to about 50 mg, about 50 mg to about 100 mg, about 100 mg to about 150 mg, about 150 mg to about 200 mg, about 200 mg to about 250 mg, about 250 mg to about 300 mg, about 300 mg to about 350 mg, about 350 mg to about 400 mg, about 400 mg to about 450 mg, or about 450 mg to about 500 mg.

BRL-37344

BRL-37344 has the chemical name (4-(2-((2-(3-chlorophenyl)-2-hydroxyethyl)amino)propyl)phenoxy)acetic acid. A pharmaceutically acceptable salt of BRL-37344 may be used. BRL-37344 may be administered via routes known in the art, such as by oral administration or subcutaneous administration. The amount of BRL-37344 or a pharmaceutically acceptable salt thereof administered to the patient can be in the range of, for example, about 1 mg to about 1000 mg per day when administered orally, or about 0.1 mg/kg body weight to about 50 mg/kg body weight per day when administered subcutaneously. In certain embodiments, BRL-37344 is administered orally at a daily dosage ranging, for example, from about 1 mg to 5 mg, about 5 mg to about 10 mg, about 10 mg to about 20 mg, about 20 mg to about 50 mg, about 50 mg to about 100 mg, about 100 mg to about 200 mg, about 200 mg to about 300 mg, about 300 mg to about 400 mg, about 400 mg to about 500 mg, about 500 mg to about 600 mg, about 600 mg to about 700 mg, about 700 mg to about 800 mg, about 800 mg to about 900 mg, or about 900 mg to about 1000 mg. In certain other embodiments, BRL-37344 is administered subcutaneously at a daily dosage ranging, for example from about 0.1 mg/kg body weight to about 0.5 mg/kg body weight, about 0.5 mg/kg body weight to about 1.0 mg/kg body weight, about 1.0 mg/kg body weight to about 2.5 mg/kg body weight, about 2.5 mg/kg body weight to about 5.0 mg/kg body weight, about 5.0 mg/kg body weight to about 7.5 mg/kg body weight, about 7.5 mg/kg body weight to about 10.0 mg/kg body weight, about 10 mg/kg body weight to about 20 mg/kg body weight, about 20 mg/kg body weight to about 30 mg/kg body weight, about 30 mg/kg body weight to about 40 mg/kg body weight, or about 40 mg/kg body weight to about 50 mg/kg body weight.

CL-316,243

CL-316,243 has the chemical name disodium 5-[(2R)-2-[[(2R)-2-(3-chlorophenyl)-2-hydroxyethyl]amino]propyl]-1,3-benzodioxole-2,2-dicarboxylate. A pharmaceutically acceptable salt of CL-316,243 may be used. The amount of CL-316,243 or a pharmaceutically acceptable salt thereof administered to the patient can be in the range of, for example, about 1 mg to about 1000 mg per day. In certain embodiments, CL-316,243 is administered (e.g., orally or subcutaneously) at a daily dosage ranging from about 1 mg to 5 mg, about 5 mg to about 10 mg, about 10 mg to about 25 mg, about 25 mg to about 50 mg, about 50 mg to about 100 mg, about 100 mg to about 200 mg, about 200 mg to about 300 mg, about 300 mg to about 400 mg, about 400 mg to about 500 mg, about 500 mg to about 600 mg, about 600 mg to about 700 mg, about 700 mg to about 800 mg, about 800 mg to about 900 mg, or about 900 mg to about 1000 mg.

GS-332

GS-332 has the chemical name sodium (2R)-[3-[3-[2-(3-chlorophenyl)-2-hydroxyethylamino]cyclohexyl]phenoxy] acetate. A pharmaceutically acceptable salt of GS-332 may be used. The amount of GS-332 or a pharmaceutically acceptable salt thereof administered to the patient can be in the range of, for example, about 1 mg to about 1000 mg per day. In certain embodiments, GS-332 is administered orally at a daily dosage ranging from about 1 mg to 5 mg, about 5 mg to about 10 mg, about 10 mg to about 25 mg, about 25 mg to about 50 mg, about 50 mg to about 100 mg, about 100 mg to about 200 mg, about 200 mg to about 300 mg, about 300 mg to about 400 mg, about 400 mg to about 500 mg, about 500 mg to about 600 mg, about 600 mg to about 700 mg, about 700 mg to about 800 mg, about 800 mg to about 900 mg, or about 900 mg to about 1000 mg.

KRP-204

KRP-204 has the chemical name 6-[2-(R)-[[2-(R)-(3-chlorophenyl)-2-hydroxyethyl]amino]propyl]-2,3-dihydro-1,4-benzodioxine-2-(R)-carboxylic acid. A pharmaceutically acceptable salt of KRP-204 may be used. KRP-204 may be administered via routes known in the art, such as by oral or ocular administration. The amount of KRP-204 or a pharmaceutically acceptable salt thereof administered to the patient can be in the range of, for example, about 1 mg to about 1000 mg per day administered orally. In certain embodiments, KRP-204 is administered orally at a daily dosage ranging from about 1 mg to 5 mg, about 5 mg to about 10 mg, about 10 mg to about 25 mg, about 25 mg to about 50 mg, about 50 mg to about 100 mg, about 100 mg to about 200 mg, about 200 mg to about 300 mg, about 300 mg to about 400 mg, about 400 mg to about 500 mg, about 500 mg to about 600 mg, about 600 mg to about 700 mg, about 700 mg to about 800 mg, about 800 mg to about 900 mg, or about 900 mg to about 1000 mg.

L-796568

L-796568 has the chemical name (R)—N-[4-[2-[[2-hydroxy-2-(3-pyridinyl)ethyl]amino]ethyl]phenyl]-4-[4-[4-(trifluoromethyl)phenyl]thiazol-2-yl]benzenesulfonamide dihydrochloride. A pharmaceutically acceptable salt of L-796568 may be used. L-796568 may be administered via routes known in the art, such as by oral administration. The amount of L-796568 or a pharmaceutically acceptable salt thereof administered to the patient can be in the range of, for example, about 1 mg to about 1000 mg per day. In certain embodiments, L-796568 is administered (e.g., orally) at a daily dosage ranging from about 1 mg to 100 mg, about 100 mg to about 200 mg, about 200 mg to about 300 mg, about 300 mg to about 400 mg, about 400 mg to about 500 mg, about 500 mg to about 600 mg, about 600 mg to about 700 mg, about 700 mg to about 800 mg, about 800 mg to about 900 mg, or about 900 mg to about 1000 mg.

It is appreciated that the beta-3-adrenergic receptor agonist may be administered by traditional routes of administration known in the art. Certain routes of administration may be preferred for a particular therapeutic agent, such as where a particular route of administration reduces first-pass metabolism or has improved bioavailability. In certain embodiments, the beta-3-adrenergic receptor agonist is administered orally, transdermally, intradermally, or by transmucosal administration alone or together in admixture with desmopressin. In yet other embodiments, the beta-3-adrenergic receptor agonist is administered orally.

The method may also be characterized according to the time period between the start of administration of desmopressin and administration of the beta-3-adrenergic receptor agonist. In certain embodiments, the first administration of desmopressin may coincide with administration of the beta-3-adrenergic receptor agonist. Alternatively, the start of administration of desmopressin may be before or after the start of administration of the beta-3-adrenergic receptor agonist. In certain embodiments, the beta-3-adrenergic receptor agonist is administered within 1 hour of the start of desmopressin administration. In certain embodiments, the beta-3-adrenergic receptor agonist is administered within 0.5 hours, 1 hour, 1.5 hours, or 2 hours of the start of desmopressin administration.

Patient Populations

The methods are contemplated to provide a therapeutic benefit to human subjects, preferably adult males, suffering from disorders associated with or featuring undesirable voiding of a patient's bladder. Exemplary disorders include nocturia, incontinence, enuresis, and diabetes insipidus. In certain embodiments, the human subject suffers from nocturia. The human subject may be an adult or a child.

Restoration of Urine Production

The methods can be further characterized according to the time period required in order for the subject to resume normal urine production after terminating administration of the desmopressin and beta-3-adrenergic receptor agonist. It is important for the subject to resume normal urine production on a daily basis so that proper fluid balance is maintained and waste can be excreted through urination. Accordingly, in certain embodiments, the method is further characterized in that urine production in the human subject is restored within about two hours after administration of desmopressin has been terminated. In certain other embodiments, the method is further characterized in that urine production in the human subject is restored within about one hour after administration of desmopressin has been terminated.

Exemplary Benefits of the Combination Therapy

The methods and compositions are contemplated to provide various benefits. One contemplated benefit is improved efficacy in inhibiting the urge to urinate in a human subject when desmopressin is administered with a beta-3-adrenergic receptor agonist compared to the efficacy observed when desmopressin is administered alone. In certain embodiments, the improvement may be a 5%, 10%, 20%, 30%, 50%, 75%, 100%, or greater improvement in inhibiting the urge to urinate in a human subject when desmopressin is administered with a beta-3-adrenergic receptor agonist compared to the efficacy observed when desmopressin is administered alone.

Another contemplated benefit is a reduction in side effects associated with administration of desmopressin. In certain embodiments, the reduction in side effects may be a 5%, 10%, 20%, 30%, 50%, 75%, 100%, or greater reduction in side effects in a human subject when desmopressin is administered with a beta-3-adrenergic receptor agonist compared to the side effects observed when desmopressin is administered alone at a dosage necessary to achieve a similar therapeutic effect.

The administration of desmopressin and a beta-3-adrenergic receptor agonist may result in a synergistic effect, e.g., a synergistic improvement in efficacy in inhibiting the urge to urinate in a human subject. In certain embodiments, the synergistic improvement in efficacy is at least a 5%, 10%, 15%, 20%, 25%, 30%, or greater improvement in efficacy compared to the additive improvement in efficacy associated with administration of desmopressin and a beta-3-adrenergic receptor agonist together.

II. Pharmaceutical Compositions and Dosing Considerations

Another aspect of the invention provides a pharmaceutical composition comprising one or more therapeutic agents described herein and a pharmaceutically acceptable carrier. The pharmaceutical compositions may be specially formulated for administration in solid or liquid form, including those adapted for the following: (1) oral administration, for example, drenches (aqueous or non-aqueous solutions or suspensions), tablets (e.g., those targeted for buccal, sublingual, and/or systemic absorption), boluses, powders, granules, pastes for application to the tongue; (2) parenteral administration by, for example, subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally. Further description of exemplary excipients and formulations designed for a particular route of administration are described below.

In certain embodiments, the invention provides a pharmaceutical composition comprising desmospressin, a beta-3-adrenergic receptor agonist, and a pharmaceutically acceptable carrier. The beta-3-adrenergic receptor agonist may be, for example, amibegron, fasobegron, mirabegron, ritobegron, solabegron, BRL-37344, CL-316,243, GS-332, KRP-204, L-796568, or a pharmaceutically acceptable salt thereof. In certain embodiments, the pharmaceutical composition is formulated for nasal administration to a human subject.

The phrase "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient. The selected dosage level will depend upon a variety of factors including the activity of the particular compound of the present invention employed, or the salt thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician having ordinary skill in the art can readily determine and prescribe the effective amount of the pharmaceutical composition required. For example, the physician could start doses of the compounds of the invention employed in the pharmaceutical composition at levels lower than that required in order to achieve the desired therapeutic effect and gradually increase the dosage until the desired effect is achieved.

Aspects of the present disclosure can also be described as follows:

1. A method of inhibiting the urge to urinate in an adult human subject over an interval of about two hours to no more than about eight hours, comprising administering to an adult human subject in need thereof an effective, low dose amount of desmopressin and a beta-3-adrenergic receptor agonist so that both exert physiological activity during an overlapping time period.

2. The method of 1, wherein the method inhibits the urge to urinate in a human subject over an interval of about 4 hours to about 7 hours.

3. The method of 1, wherein an antidiuretic effect is achieved over an interval of about two hours to no more than about six hours.

4. The method of 1, wherein an antidiuretic effect is achieved over an interval of about four hours to no more than about seven hours.

5. The method of any one of 1-4, wherein the administering achieves in the subject a blood plasma concentration of desmopressin that does not exceed 10 or 15 pg/mL.

6. The method of any one of 1-4, wherein the administering achieves in the subject a blood plasma concentration of desmopressin in the range of about 0.5 pg/mL to about 5 pg/mL.

7. The method of any one of 1-4, wherein the administering achieves in the human subject a blood plasma concentration of desmopressin in the range of about 0.5 pg/mL to about 2.5 pg/mL.

8. The method of any one of 1-7, wherein desmopressin is administered transdermally, intradermally, or transmucosally across the oral or nasal mucosa.

9. The method of any one of 1-7, wherein desmopressin is administered transdermally or intradermally.

10. The method of any one of 1-7, wherein desmopressin is administered intranasally.

11. The method of any one of 1-7, wherein desmopressin is administered sublingually across the oral mucosa.

12. The method of 9, wherein desmopressin is administered at a flux rate ranging from about 5 ng/hour to about 35 ng/hour.

13. The method of 9, wherein desmopressin is administered at a flux rate ranging from about 5 ng/hour to about 15 ng/hour.

14. The method of any one of 1-13, wherein the beta-3-adrenergic receptor agonist is amibegron, fasobegron, mirabegron, ritobegron, solabegron, BRL-37344, CL-316,243, GS-332, KRP-204, L-796568, or a pharmaceutically acceptable salt thereof.

15. The method of any one of 1-13, wherein the beta-3-adrenergic receptor agonist is amibegron, fasobegron, or solabegron.

16. The method of any one of 1-13, wherein the beta-3-adrenergic receptor agonist is mirabegron.

17. The method of any one of 1-16, wherein the beta-3-adrenergic receptor agonist is administered orally, transdermally, intradermally, or across the nasal or oral mucosa.

18. The method of any one of 1-16, wherein the beta-3-adrenergic receptor agonist is administered orally.

19. The method of any one of 1-18, wherein the beta-3-adrenergic receptor agonist is administered within 1 hour before or after the start of desmopressin administration.

20. The method of any one of 1-19, wherein the subject suffers from nocturia, incontinence, enuresis, or diabetes insipidus.

21. The method of any one of 1-19, wherein the subject suffers from nocturia.

22. The method of any one of 1-21, wherein urine production in the human subject is restored within about two hours after administration of desmospressin has been terminated.

23. The method of 1, wherein the method comprises administering to the adult human subject a beta-3-adrenergic receptor agonist on a daily basis for a period of at least a month and administering desmopressin before the subject retires to sleep.

24. The method of 1, wherein the method comprises administering to the adult human subject a beta-3-adrenergic receptor agonist at a dose level lower than its smallest drug label recommended dose for treatment of BPH and administering desmopressin before the subject retires to sleep.

25. The method of 1, wherein the method comprises administering to the adult human subject as a mixture before the subject retires to sleep desmopressin and a beta-3-adrenergic receptor agonist at a dose level lower than the smallest drug label recommended dose of said agonist for treatment of BPH.

26. A pharmaceutical composition comprising desmopressin, a beta-3-adrenergic receptor agonist, and a pharmaceutically acceptable carrier.

27. The pharmaceutical composition of 26, wherein the pharmaceutical composition is formulated for intranasal or sublingual administration to a human subject.

28. The pharmaceutical composition of 26 or 27, wherein the beta-3-adrenergic receptor agonist is amibegron, fasobegron, mirabegron, ritobegron, solabegron, BRL-37344, CL-316,243, GS-332, KRP-204, L-796568, or a pharmaceutically acceptable salt thereof.

EXAMPLES

The invention now being generally described, will be more readily understood by reference to the following examples, which are included merely for purposes of illustration of certain aspects and embodiments of the present invention, and are not intended to limit the invention.

Example 1

Part I—Experimental Procedures

Patients in the clinical study met the following criteria: (a) male or female that were at least 50 years old and experiencing on average at least two nocturnal voids per night for a duration of at least six months, and (b) do not suffer from any of congestive heart failure, diabetes insipidus, renal insufficiency, hepatic insufficiency, incontinence, illness requiring systemic steroids, malignancy within the past 5 years, sleep apnea, nephrotic syndrome, unexplained pelvic mass, urinary bladder neurological dysfunction, have undergone urinary bladder surgery or radiotherapy, or are pregnant or breast feeding.

Patients received as a nasal spray either (i) a 1.5 μg dosage of desmopressin or (ii) placebo. The desmopressin nasal spray (or placebo) was administered daily just prior to bedtime for a duration of twelve weeks. The desmopressin nasal spray was prepared by combining aliquots of an Emulsion Stock Solution and a Buffer Solution as described below.

Emulsion Stock Solution: To produce an emulsion stock solution, the following ingredients in parts by weight are added to a vessel equipped with a stirring bar, and mixed for 15 minutes at 60-65° C.: (i) 180 parts sorbitan monolaurate (Span-20) aqueous solution (12 mg/mL); (ii) 30 parts Polysorbate 20 (Tween-20) aqueous solution (2 mg/mL); (iii) 400 parts cottonseed oil aqueous emulsion (26.6 mg/mL); (iv) 600 parts cyclopentadecanolide (CPE-215) aqueous emulsion (40 mg/mL); and (v) water to produce 1,500 grams total batch size. After mixing, the preparation is homogenized using a high speed mixture at 6500 RPM+ for 20-25 minutes to produce a fine emulsion. This solution is autoclaved to assure sterility.

Buffer Solution: To produce a citric acid buffer stock solution, the following ingredients in parts by weight are added to a vessel equipped with a stirring bar, and mixed for 5 minutes at 60-65° C.: (i) 6200 parts water; (ii) 16 parts anhydrous citric acid aqueous solution (1.85 mg/mL); (iii) 76 parts sodium citrate, dihydrate aqueous solution (8.9 mg/mL); (iv) 104 parts Polysorbate 20 (Tween-20) aqueous solution (12 mg/mL); and (v) water to produce 8,500 grams total batch size.

Desmopressin Stock Solution: To produce a desmopressin stock solution, 0.111 part desmopressin acetate trihydrate is added to sufficient buffer stock solution to produce 100.0 mL of solution, and stirred until all the desmopressin is dissolved to produce a stock solution having a concentration of 100 μg desmopressin/mL. From this stock solution a 30 μg/mL solution was prepared by dilution.

Desmopressin Nasal Spray: To produce the desmopressin nasal spray, aliquots of the 30 μg/mL solution were filtered to eliminate any bacterial contamination and diluted with an equal volume of emulsion stock solution to produce aseptic, preservative free dose forms comprising 15 μg/mL desmopressin, pH 5.5, containing 2% cyclopentadecanolide. These were bottled in sterile pump spray bottles fitted with a Pfeiffer APF pump sprayers that deliver 100 μL per metered spray (i.e., 1.5 μg desmopressin (i.e., 1500 ng desmopressin) per spray). The liquid contains no detectable microorganisms.

Desmopressin Therapy in Combination with Mirabegron:

A female post-menopausal patient receive desmopressin therapy nasal spray as described above in combination with mirabegron (trade name Myrbetriq®) extended release tablets. Prior to the therapy, the patient reported greater than two nocturic episodes per day. At day 29 and day 43 after starting therapy, the patient reported less than one nocturic episode every two days.

III. Medical Kits

Another aspect of the invention provides a kit for inhibiting the urge to urinate in a human subject or inducing an antidiuretic effect in a human subject. The kit comprises (i) instructions for use (ii) desmopressin and (iii) a beta-3-adrenergic receptor agonist, present in mixture or separately, and if separate, administered differently, e.g., orally for the agonist and transmucosally or by way of a skin patch for the desmopressin.

The description above describes multiple aspects and embodiments of the invention, including therapeutic methods, pharmaceutical compositions, and medical kits. The patent application specifically contemplates all combinations and permutations of the aspects and embodiments.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A method of inhibiting the urge to urinate in an adult human subject over an interval of about two hours to no more than about eight hours, comprising administering to the adult human subject in need thereof a pharmaceutical composition comprising pharmaceutically active agents, the pharmaceutically active agents consisting of an effective, low dose amount of desmopressin and a beta-3-adrenergic receptor agonist so that both exert physiological activity during an overlapping time period, wherein the beta-3-adrenergic receptor agonist is administered at a daily dosage of about 1 mg to about 20 mg.

2. The method of claim 1, wherein the method inhibits the urge to urinate in a human subject over an interval of about 4 hours to about 7 hours.

3. The method of claim 1, wherein an antidiuretic effect is achieved over an interval of about two hours to no more than about six hours.

4. The method of claim 1, wherein the administering achieves in the subject a blood plasma concentration of desmopressin that does not exceed 15 pg/mL.

5. The method of claim 1, wherein the administering achieves in the subject a blood plasma concentration of desmopressin in the range of about 0.5 pg/mL to about 5 pg/mL.

6. The method of claim 1, wherein the pharmaceutical composition is administered transdermally or intradermally.

7. The method of claim 1, wherein the pharmaceutical composition is administered intranasally.

8. The method of claim 1, wherein the pharmaceutical composition is administered sublingually across the oral mucosa.

9. The method of claim 1, wherein the beta-3-adrenergic receptor agonist is amibegron, fasobegron, mirabegron, ritobegron, solabegron, BRL-37344, CL-316,243, GS-332, KRP-204, L-796568, or a pharmaceutically acceptable salt thereof.

10. The method of claim 1, wherein the beta-3-adrenergic receptor agonist is mirabegron.

11. The method of claim 1, wherein the pharmaceutical composition further comprises a pharmaceutically acceptable carrier.

12. The method of claim 1, wherein the beta-3-adrenergic receptor agonist is administered at a daily dosage ranging from 1 mg to 5 mg.

13. The method of claim 1, wherein the beta-3-adrenergic receptor agonist is administered at a daily dosage ranging from 5 mg to 10 mg.

14. The method of claim 1, wherein the beta-3-adrenergic receptor agonist is administered at a daily dosage ranging from 10 mg to 20 mg.

15. The method of claim 12, wherein the beta-3-adrenergic receptor agonist is mirabegron.

16. The method of claim 13, wherein the beta-3-adrenergic receptor agonist is mirabegron.

17. The method of claim 14, wherein the beta-3-adrenergic receptor agonist is mirabegron.

18. The method of claim 1, wherein the desmopressin is administered in an amount that delivers to the blood stream a concentration of desmopressin no more than 2 ng/kg.

19. The method of claim 12, wherein the desmopressin is administered in an amount that delivers to the blood stream a concentration of desmopressin no more than 2 ng/kg.

20. The method of claim 13, wherein the desmopressin is administered in an amount that delivers to the blood stream a concentration of desmopressin no more than 2 ng/kg.

21. The method of claim 14, wherein the desmopressin is administered in an amount that delivers to the blood stream a concentration of desmopressin no more than 2 ng/kg.

22. The method of claim 1, wherein the adult human subject suffers from adult primary nocturnal enuresis, overactive bladder, incontinence, nocturia, or urinary urgency or frequency during waking hours.

* * * * *

UNITED STATES PATENT AND TRADEMARK OFFICE
CERTIFICATE OF CORRECTION

PATENT NO. : 10,568,927 B2  
APPLICATION NO. : 15/811384  
DATED : February 25, 2020  
INVENTOR(S) : S. H. Fein et al.

Page 1 of 1

It is certified that error appears in the above-identified patent and that said Letters Patent is hereby corrected as shown below:

In the Claims

In Claim 4, at Column 23, Line 24, replace "desmopres sin" with --desmopressin--.

In Claim 18, at Column 24, Line 25, replace "desmopres sin" with --desmopressin--.

In Claim 19, at Column 24, Line 28, replace "desmopres sin" with --desmopressin--.

In Claim 20, at Column 24, Line 29, replace "desmopres sin" with --desmopressin--.

In Claim 20, at Column 24, Line 31, replace "desmopres sin" with --desmopressin--.

In Claim 21, at Column 24, Line 32, replace "desmopres sin" with --desmopressin--.

In Claim 21, at Column 24, Line 34, replace "desmopres sin" with --desmopressin--.

Signed and Sealed this  
Fifteenth Day of September, 2020

Andrei Iancu  
*Director of the United States Patent and Trademark Office*